(12) United States Patent
Govari et al.

(10) Patent No.: US 8,979,835 B2
(45) Date of Patent: Mar. 17, 2015

(54) SENSING CONTACT OF ABLATION CATHETER USING DIFFERENTIAL TEMPERATURE MEASUREMENTS

(71) Applicant: Biosense Webster (Israel), Ltd., Yokneam (IL)

(72) Inventors: Assaf Govari, Haifa (IL); Christopher Thomas Beeckler, Brea, CA (US); Athanassios Papaioannou, Los Angeles, CA (US)

(73) Assignee: Biosense Webster (Israel) Ltd. (IL)

( * ) Notice: Subject to any disclaimer, the term of this patent is extended or adjusted under 35 U.S.C. 154(b) by 0 days.

(21) Appl. No.: 13/764,867

(22) Filed: Feb. 12, 2013

(65) Prior Publication Data

US 2013/0158548 A1    Jun. 20, 2013

Related U.S. Application Data

(62) Division of application No. 12/646,165, filed on Dec. 23, 2009.

(51) Int. Cl.
| | | |
|---|---|---|
| *A61B 18/18* | (2006.01) | |
| *A61B 18/14* | (2006.01) | |
| *A61B 17/32* | (2006.01) | |
| *A61B 18/20* | (2006.01) | |
| *A61B 18/00* | (2006.01) | |

(52) U.S. Cl.
CPC ..... *A61B 18/1492* (2013.01); *A61B 17/320068* (2013.01); *A61B 18/20* (2013.01); *A61B 2018/00011* (2013.01); *A61B 2018/00797* (2013.01); *A61B 2018/00821* (2013.01)
USPC .............................................. 606/34; 606/41

(58) Field of Classification Search
USPC ................................................ 606/32–34, 41
See application file for complete search history.

(56) References Cited

U.S. PATENT DOCUMENTS

| | | | |
|---|---|---|---|
| 5,542,915 | A | 8/1996 | Edwards et al. |
| 5,688,267 | A | 11/1997 | Panescu et al. |

(Continued)

FOREIGN PATENT DOCUMENTS

| | | | |
|---|---|---|---|
| JP | 2008-80152 A | | 4/2008 |
| WO | 00/15130 | | 3/2000 |

OTHER PUBLICATIONS

European Search Report mailed on Apr. 7, 2011 from corresponding European Patent Application No. 10252184.6.

(Continued)

*Primary Examiner* — Linda C. Dvorak
*Assistant Examiner* — Jocelyn D Ram

(57) ABSTRACT

Tissue ablation is carried out using insertion tube having at least one ablation electrode, a first temperature sensor disposed on the distal portion sufficiently proximate the ablation electrode to detect heat generated during the ablation procedure, a second temperature sensor disposed on the distal portion sufficiently distant from the ablation electrode to be unable to detect the heat, and electronic logic circuitry linked to the first temperature sensor and the second temperature sensor and programmed to compute a temperature differential between respective temperatures sensed by the first temperature sensor and the second temperature sensor when conveying the electromagnetic energy. Satisfactory contact status between the ablation electrode and the target tissue is indicated when the temperature differential exceeds a predetermined threshold.

5 Claims, 4 Drawing Sheets

(56) References Cited

U.S. PATENT DOCUMENTS

| | | | |
|---|---|---|---|
| 5,735,846 A | 4/1998 | Panescu et al. | |
| 5,769,847 A * | 6/1998 | Panescu et al. | 606/42 |
| 5,849,028 A * | 12/1998 | Chen | 607/102 |
| 6,042,580 A * | 3/2000 | Simpson | 606/32 |
| 6,226,542 B1 | 5/2001 | Reisfeld | |
| 6,264,653 B1 * | 7/2001 | Falwell | 606/41 |
| 6,301,496 B1 | 10/2001 | Reisfeld | |
| 6,312,425 B1 | 11/2001 | Simpson et al. | |
| 6,332,089 B1 | 12/2001 | Acker et al. | |
| 6,356,790 B1 * | 3/2002 | Maguire et al. | 607/102 |
| 6,618,612 B1 | 9/2003 | Acker et al. | |
| 6,690,963 B2 | 2/2004 | Ben-Haim et al. | |
| 6,814,733 B2 | 11/2004 | Leatham et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 2004/0068178 A1 | 4/2004 | Govari | |
| 2004/0102769 A1 | 5/2004 | Schwartz et al. | |
| 2004/0147920 A1 | 7/2004 | Keidar | |
| 2008/0161797 A1 * | 7/2008 | Wang et al. | 606/41 |
| 2008/0281312 A1 | 11/2008 | Werneth et al. | |
| 2009/0076495 A2 * | 3/2009 | Dando et al. | 606/34 |
| 2011/0218526 A1 * | 9/2011 | Mathur | 606/33 |

OTHER PUBLICATIONS

Australian Exam Report mailed on Feb. 7, 2014 from corresponding Australian Patent Application No. 2010257206.
Japanese Notification of Reasons for Refusal dated Jul. 15, 2014 in corresponding Japanese Patent Application No. 2010-285651.

* cited by examiner

SENSING CONTACT OF ABLATION CATHETER USING DIFFERENTIAL TEMPERATURE MEASUREMENTS

This application is a divisional of U.S. application Ser. No. 12/646,165 filed Dec. 23, 2009, the complete disclosure of which is hereby incorporated herein by reference for all purposes.

BACKGROUND OF THE INVENTION

1. Field of the Invention

This invention relates to tissue ablation systems. More particularly, this invention relates to monitoring of contact between an invasive probe and tissue within the body.

2. Description of the Related Art

Cardiac arrhythmia, such as atrial fibrillation, occurs when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

SUMMARY OF THE INVENTION

During ablation, parts of the catheter that are in contact with tissue typically become considerably hotter than parts that are in contact only with blood. Embodiments of this invention take advantage of this phenomenon to verify proper electrode contact with the tissue.

An embodiment of the invention provides a medical apparatus including an insertion tube, at least one ablation electrode disposed on the distal portion thereof for conveying electromagnetic energy to a target tissue during an ablation procedure, a first temperature sensor disposed on the distal portion sufficiently proximate the ablation electrode to detect heat generated during the ablation procedure, and a second temperature sensor disposed on the distal portion sufficiently distant from the ablation electrode to be less able or even unable to detect the heat. Electronic logic circuitry linked to the first temperature sensor and the second temperature sensor is programmed to compute a temperature differential between respective temperatures sensed by the first temperature sensor and the second temperature sensor when conveying the electromagnetic energy, and to indicate a satisfactory contact status between the ablation electrode and the target tissue when the temperature differential exceeds a predetermined threshold.

According to an aspect of the apparatus, the electronic logic circuitry is programmed to indicate an unsatisfactory contact status between the ablation electrode and the target tissue when the temperature differential fails to exceed the predetermined threshold.

According to still another aspect of the apparatus, the insertion tube is a lasso catheter.

According to one aspect of the apparatus, the electronic logic circuitry is programmed to compute a first temperature differential and a second temperature differential when relatively high and low flows of coolant are applied to the ablation electrode, respectively, wherein the electronic logic circuitry is programmed to indicate an unsatisfactory contact status between the ablation electrode and the target tissue when a difference between the first temperature differential and the second temperature differential fails to exceed the predetermined threshold.

According to an aspect of the apparatus, the first temperature sensor and the second temperature sensor are thermocouples.

A further aspect of the apparatus includes an ablation power generator coupled to the ablation electrode to supply the energy thereto.

According to yet another aspect of the apparatus, the insertion tube is configured for insertion through a blood vessel into a heart of a subject for ablation of myocardial tissue in the heart.

Other embodiments of the invention provide methods for carrying out the operations performed by the apparatus.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Figure 1:
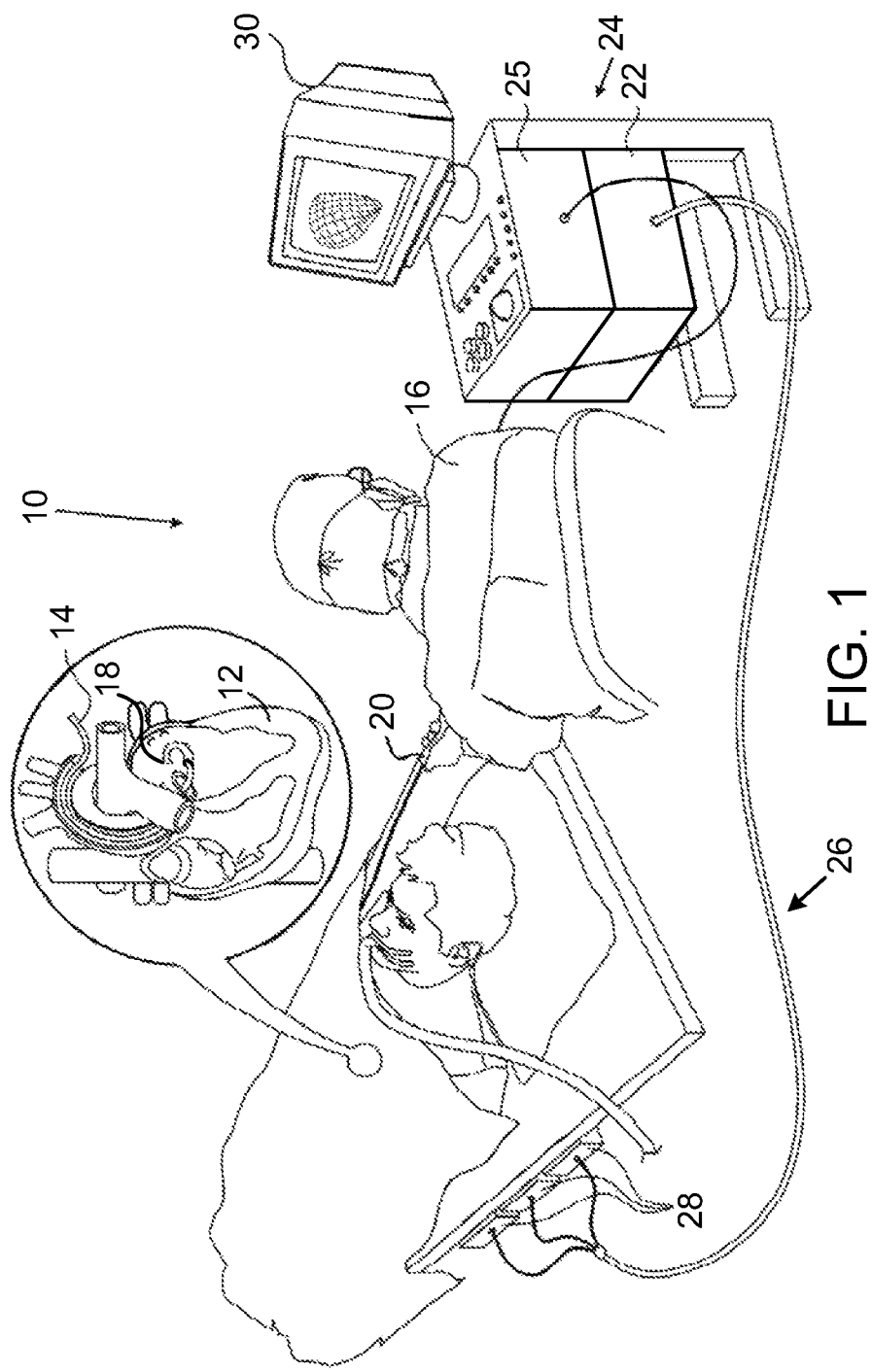
FIG. 1 is a pictorial illustration of a system for detecting areas of abnormal electrical activity and performing ablative procedures in a heart of a living subject in accordance with a disclosed embodiment of the invention.

Turning now to the drawings, reference is initially made to FIG. 1, which is a pictorial illustration of a system 10 for performing ablative procedures on a heart 12 of a living subject in accordance with a disclosed embodiment of the invention. The system comprises a catheter 14, such as a lasso catheter, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892, 091, whose disclosure is herein incorporated by reference. Although the embodiment described with respect to FIG. 1 is concerned primarily with cardiac ablation, the principles of the invention may be applied, mutatis mutandis, to other catheters and probes and to body tissues other than the heart.

Areas determined to be abnormal by evaluation of the electrical activation maps can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention can be applied to different heart chambers, and to mapping in sinus rhythm, and when many different cardiac arrhythmias are present.

The catheter 14 typically comprises a handle 20, having suitable controls to enable the operator 16 to steer, position and orient the distal end of the catheter as desired for the ablation. To aid the operator 16, the distal portion of the catheter 14 contains position sensors (not shown) that provide signals to a positioning processor 22, located in a console 24. The console 24 typically contains an ablation power generator 25. The catheter 14 may be adapted to conduct ablative energy to the heart using any known ablation technique, e.g., radiofrequency energy, ultrasound energy, and laser energy. Such methods are disclosed in commonly assigned U.S. Pat. Nos. 6,814,733, 6,997,924, and 7,156,816, which are herein incorporated by reference.

The positioning processor 22 is an element of a positioning system 26 that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning system 26 comprises a magnetic position tracking system that determines the position of the catheter 14. The positioning system 26 generates magnetic fields in a predefined working volume its vicinity and senses these fields at the catheter. The positioning system 26 typically comprises a set of external radiators, such as field generating coils 28, which are located in fixed, known positions external to the patient. The coils 28 generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking systems that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning system 26 shown in FIG. 1 uses magnetic fields, the methods described below may be implemented using any other suitable positioning system, such as systems based on electromagnetic fields, acoustic or ultrasonic measurements. The positioning system 26 may be realized as the CARTO XP EP Navigation and Ablation System, available from Biosense Webster, Inc., 3333 Diamond Canyon Road, Diamond Bar, Calif. 91765.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 30. The signal processing circuits typically receive, amplify, filter and digitize signals from the catheter 14, including signals generated by the sensors (not shown) and a plurality of sensing electrodes 36. The digitized signals are received and used by the console 24 to compute the position and orientation of the catheter 14 and to analyze the electrical signals from the electrodes. The information derived from this analysis is used to generate an electrophysiological map of at least a portion of the heart 12 or structures such as the pulmonary venous ostia for diagnostic purposes, such as locating an arrhythmogenic area in the heart or to facilitate therapeutic ablation.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 maintained in a fixed position relative to the heart 12. By comparing the position of the catheter 14 to that of the reference catheter, the coordinates of catheter 14 are determined relative to the heart 12, irrespective of heart motion. Alternatively, any other suitable method may be used to compensate for heart motion. Nevertheless, the positioning system 26 cannot guarantee that an energy-conveying component of the catheter 14 is in actual contact with the tissue to be ablated.

The Catheter

Figure 2:
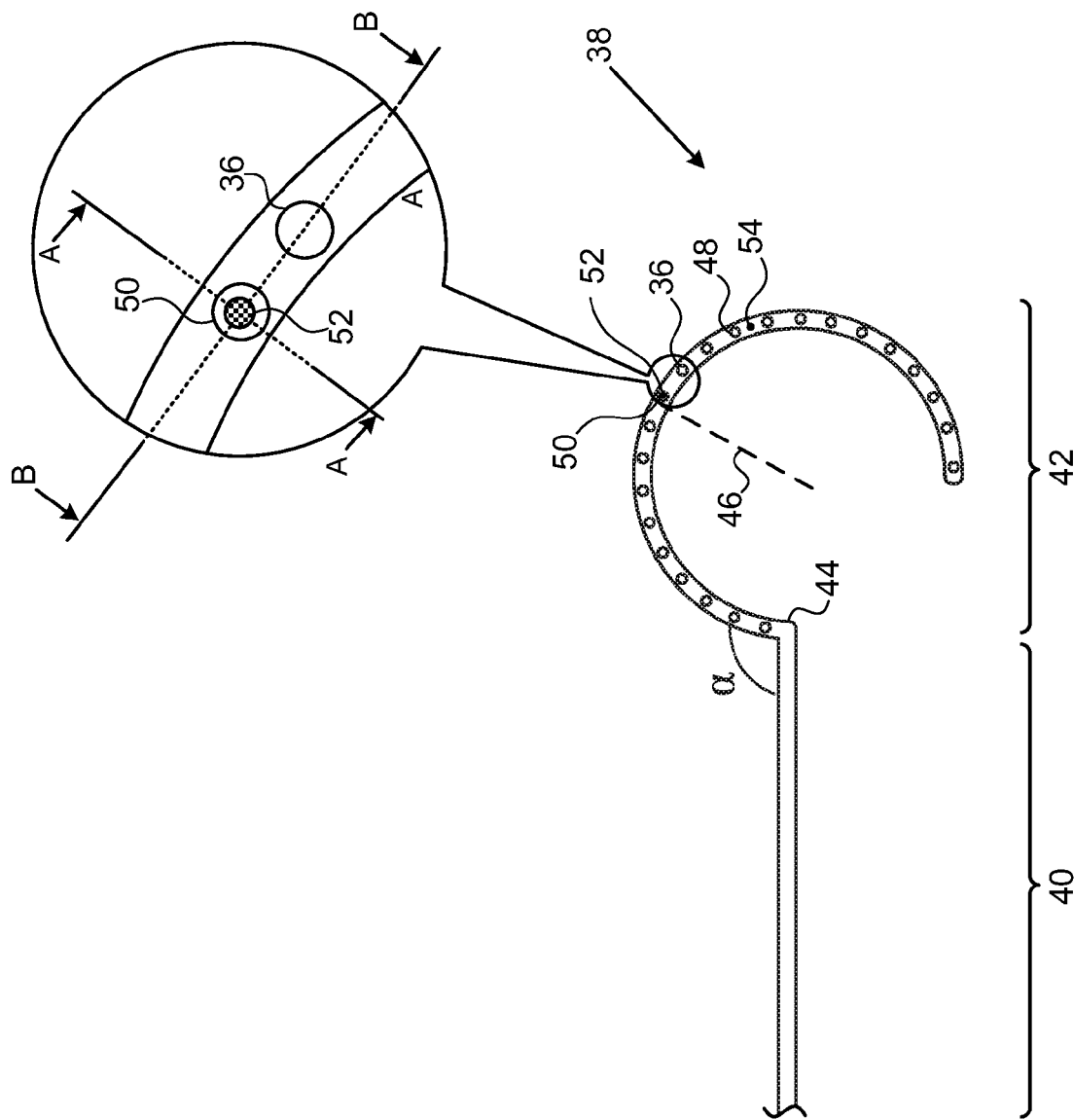
FIG. 2 is an elevation of a lasso catheter that is constructed and operative in accordance with a disclosed embodiment of the invention.

Reference is now made to FIG. 2, which is an elevation of a lasso catheter 38 that is constructed and operative in accordance with a disclosed embodiment of the invention. It is to be emphasized that in the following discussion, a lasso catheter is presented by way of example. The principles of the invention may equally be applied to ablation catheters having many configurations. For example, temperature sensors may be placed on opposing sides of other sorts of catheters and other ablation devices. In a further example, the temperature sensors may be fixed on opposite sides along the length of a multielectrode catheter that is used for linear ablation.

The catheter 38 is a steerable device. Its handle, control and steering mechanisms (not shown) are conventional and are omitted from FIG. 2 for simplicity. The catheter 38 features a base segment 40, which is bendable responsively to forces applied by the steering mechanisms. A distal loop segment 42 completes the lasso configuration. The loop segment 42 is joined to the base segment 40 by a range-restricted angle α at a joint 44. The angle a between the loop segment 42 and the base segment 40 optimally is about 90 degrees. The joint 44 may define a point where two initially-separate members (base segment 40; loop segment 42) are joined, or, alternatively, the joint 44 may define a point on the catheter 38 where a single member is bent, so as to form the base segment 40 and the loop segment 42. The loop segment 42 is of a known fixed length, having a curvature dimensioned to a particular medical application. The curvature may be adjustable using the steering and control mechanisms (not shown) of the catheter. A radius 46, adjustable between 7-15 mm, is suitable for cardiac applications. However, the radius 46 may vary up to 25 mm in some applications. In any case, the loop segment 42 may be dimensioned so as to conform to structures such as the ostia of pulmonary veins or the coronary sinus.

The loop segment 42 is constructed of a material that preferably is twistable but not stretchable when subjected to typical forces encountered in medical practice. Preferably, the loop segment 42 is sufficiently resilient so as to assume a predetermined curved form, i.e., an open circular or semicircular form when no force is applied thereto, and to be deflected from the predetermined curved form when a force is applied thereto. Preferably, the loop segment 42 has an elasticity that is generally constant over at least a portion of its length, for example, because of internal reinforcement of the curved section with a resilient longitudinal member, as is known in the art. The loop segment 42 may be made from polyurethane and be at least one mm in diameter.

One or more electrodes, indicated representatively as electrodes 36, 48, 50, are disposed on the loop segment 42, and may be assigned ablation and mapping functions in many combinations. Ablation electrodes 36, 48 are associated with temperature sensors 52, 54. The sensors are conventional miniature thermocouples. American Wire Gauge (AWG) 46 is suitable. Coolant is delivered conventionally, e.g., via accessory ports (not shown), to the ablation electrodes at a flow during operation of about 30-40 ml/min.

Mapping electrode 36 is not associated with temperature sensor. Electrodes 36, 48, 50 are shown as having a circular configuration, but this is not critical. Many different types of electrodes can be used in various combinations, e.g., a tip ablation electrode, ring electrodes, or coil electrodes, so long as the ablation electrodes are sufficiently close to one temperature sensor, enabling the one sensor to detect increased temperature in the target tissue during ablation and sufficiently spaced apart from another temperature sensor, such that the other temperature sensor does not detect the increased temperature in the target tissue or detects it to a lesser extent than the one electrode. The other temperature sensor is sometimes referred to as a "reference temperature sensor".

Figure 3:
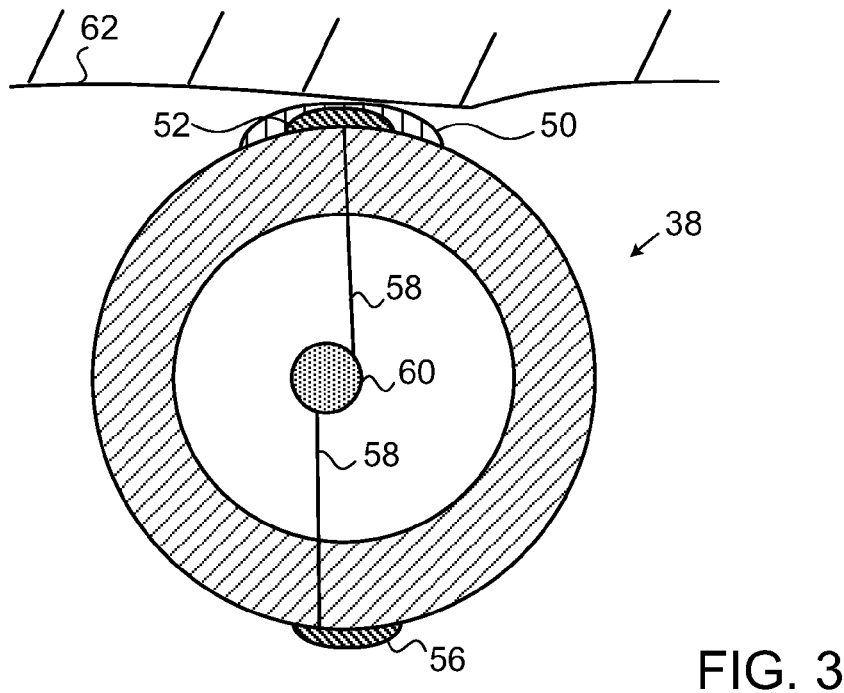
FIG. 3 is a sectional view through the loop segment of the catheter shown in FIG. 2 taken through line A-A, in accordance with a disclosed embodiment of the invention.

Reference is now made to FIG. 3, which is a sectional view of the catheter 14 through the loop segment 42 of the catheter 38 (FIG. 2) taken through line A-A. Electrode 50 diametrically opposes sensor 56, which is not seen on FIG. 2. The sensors 52, 56 are connected by wires 58 to a cable 60 that extends proximally and conveys signals to the console 24 (FIG. 1). It will be apparent that when the sensor 52 is in contact with endocardium 62, the sensor 56 is not in contact with the tissue, but is irrigated by blood. The temperature sensors 52, 56 can be disposed in different configurations, and need not necessarily be diametrically opposed as shown in FIG. 3. However, when one or more of the ablation electrodes 36, 48 is operationally engaged with target tissue, the sensor 52 is intended to respond to heat generated by ablation and the sensor 56 is not intended to so respond. Therefore, sensors 52, 56 should be sufficiently spaced apart such that when temperature readings are taken during a normally proceeding ablation procedure, the sensor 56 is less responsive to heat generated at the ablation site than the sensor 52. The sensor 56 should read at least 2-3° C. lower than the sensor 54.

Figure 4:
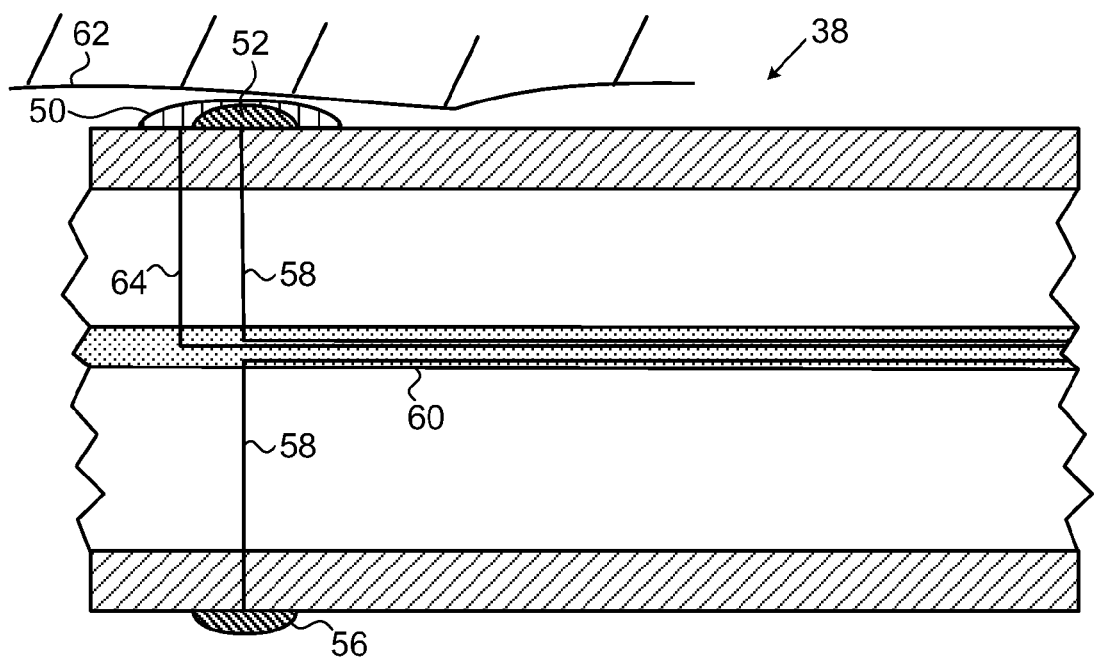
FIG. 4 is a fragmentary sectional view through the loop segment of the catheter shown in FIG. 2 taken through line B-B, in accordance with a disclosed embodiment of the invention.

Reference is now made to FIG. 4, which is a fragmentary sectional view of the catheter 14 through the loop segment 42 of the catheter 38 (FIG. 2) taken through line B-B. Electrode 50 is shown in relation to sensor 52. A wire 64 conducts ablation currents from the console 24 (FIG. 1) to the electrode 50 via the cable 60.

The catheter 38 may be adapted to ablate a circular path within one of the pulmonary veins. The loop segment 42 (FIG. 2) fits into the ostium of the vein, so that ablation electrodes disposed on the outside of the lasso contact the inner circumference of the vein. The inside of the lasso does not contact tissue, but is rather irrigated by blood flow through the vein. As best seen in the example of FIG. 4, ablation energy is conducted through the electrode 50 into the target tissue 62, e.g., endocardium or the intima of a pulmonary vein. If the catheter 38 is in contact with the target tissue 62, the sensor 52 is preferably also in contact or near contact with the target tissue 62. In any case, the sensor 52 should be disposed sufficiently close to the electrode 50 such that heat generated in the target tissue 62 is detected by the sensor 52. It is recommended to mount the sensor 52 on the internal side of the electrode. The sensor 56 is located away from the electrode 50, and does not detect the heat, but acts as a reference temperature sensor. The sensor 52 reports a higher temperature reading than the sensor 56 to the console 24 (FIG. 1). A threshold temperature differential exceeding 10-15 degrees C. is an indication to the operator that the catheter 38 is properly positioned in contact with the target tissue 62. Typically the sensor 56 is diametrically opposite the sensor 52 on the shaft of the catheter 38, as shown in FIG. 3. An arc of at least 90 degrees should separate the sensor 52 from the sensor 56 to assure that the sensor 56 does not sense the heat generated in the target tissue 62.

Contrarily, a temperature differential less than the threshold is an indication to the operator that the catheter 38 is not properly positioned in contact with the target tissue 62. In such a case, the ablation current may be turned off, and the lasso may be repositioned before continuing the procedure.

Electronic logic circuitry, e.g., a computer, in the console 24 (FIG. 1) is programmed to compute a temperature differential between respective temperatures sensed by the sensor 52, 56 when conveying electromagnetic energy to the electrode 50, and to record a contact status between the electrode 50 and the target tissue 62 responsively to the temperature differential.

Alternate Embodiments

In the embodiment of FIG. 2, each ablation electrode is associated with a respective pair of temperature sensors—one closely located and the other more distantly located. In other embodiments, each ablation electrode continues to be associated with respective closely located temperature sensors. However the readings of these sensors are compared with a common reference temperature sensor, which is spaced apart from all the ablation electrodes.

Further alternatively, more than one reference temperature sensor may be employed, so long as none is close enough to an ablation electrode to produce a misleading reading caused by target tissue heating. In this embodiment the number of reference temperatures sensors is smaller than the number of ablation electrodes.

An advantage of using one reference temperature sensor or a small number of reference temperature sensors is cost and simplicity of construction. Use of a larger number of reference electrodes, while requiring a more complex construction, e.g., more internal wiring, permits detection of spurious readings in a reference temperature sensor. This can be dealt with by employing arbitration logic in the console 24 (FIG. 1).

Operation

Figure 5:
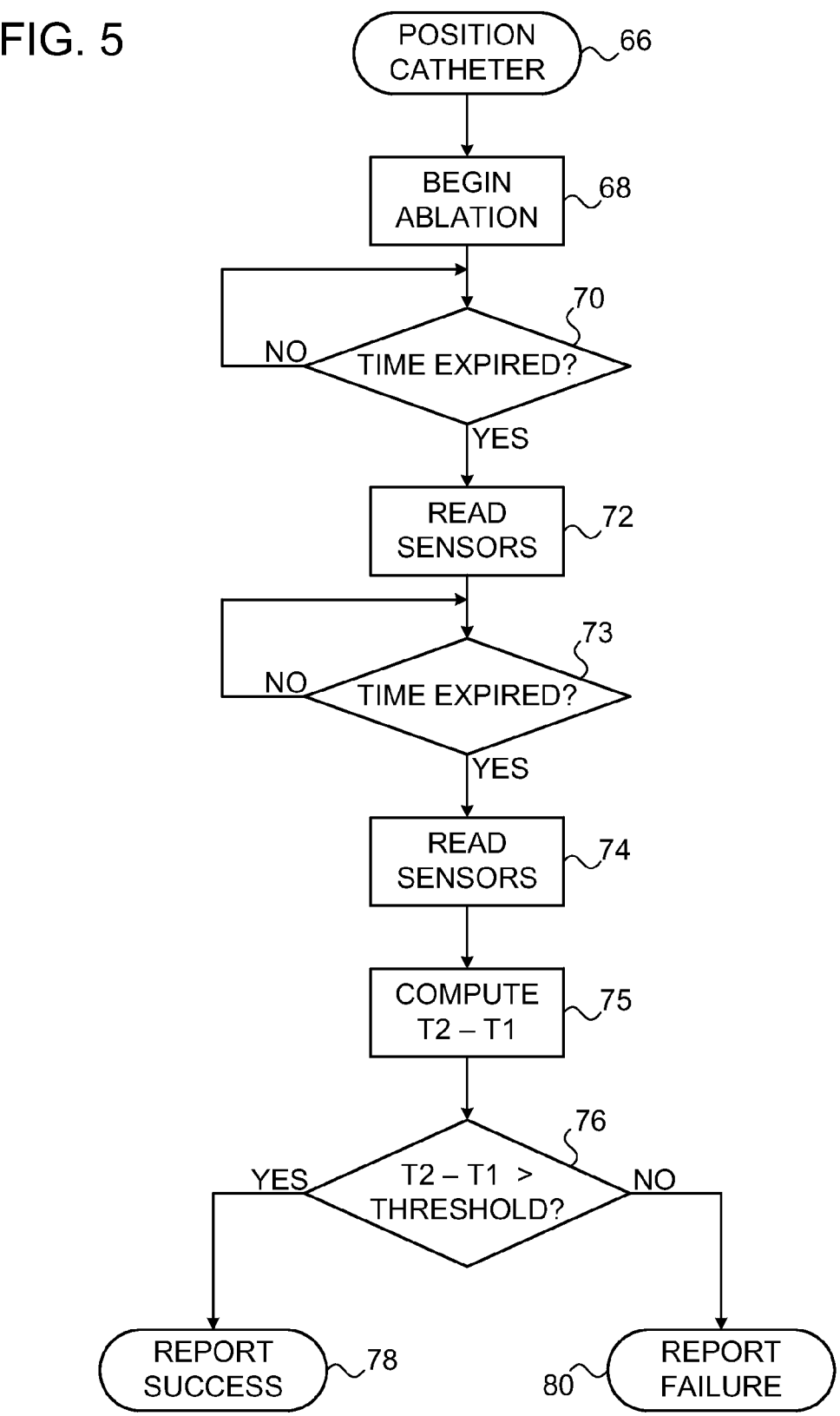
FIG. 5 is a flow chart of a method of cardiac ablation in accordance with a disclosed embodiment of the invention.

Reference is now made to FIG. 5, which is a flow chart of a method of cardiac ablation in accordance with a disclosed embodiment of the invention. At initial step 66 a catheter, constructed in accordance with one of the above-described embodiments, is introduced into the heart, and an ablation electrode, together with its associated temperature sensor, is positioned at a target site using the positioning system 26 (FIG. 1).

Next, at step 68 ablation of the target is initiated by enabling the ablation power generator 25. During ablation the ablation electrode is cooled conventionally using a flow of coolant in the range of 30-40 ml/min.

Temperature readings are taken twice from the temperature sensors. A delay is initiated prior to the first reading, at delay step 70 for a predetermined time interval, typically about 2-3 sec. During this delay interval, the flow of coolant is reduced to a minimal value, about 4 ml/min. This allows heat buildup to occur in the target tissue if the ablation electrode is in proper contact with the target tissue.

Next, at step 72 the first temperature readings are taken from the temperature sensor associated with the ablation electrode and from one or more reference temperature sensors. The readings may be averaged or arbitrated among the temperature sensors (when they disagree). In any case, the result is a temperature reading T1. When the first readings are completed, the coolant flow is restored 30-40ml/ml.

Next, at delay step 73, lasting about 2-3 seconds, the temperature re-equilibrates. Then at step 74, the temperature sensors are read a second time to obtain a temperature reading T2.

Next, at step 75 the temperature differential (T2–T1) is computed. If ablation has been proceeding normally, i.e., there was sufficient contact between the ablation electrode and the ablation site, a temperature difference T2–T1 of at least 10-15° C. is expected. However, If there were no ablation then the difference T2–T1 would be insignificant.

If desired, the temperature readings T2 and T1 may be taken in reverse order, so long as one reading is taken with minimal cooling of the ablation electrode and the other with normal cooling.

Useful information can be gained even from the first reading in step 72. If the temperature differential between the temperature sensors 52, 56 exceeds a threshold, it is possible to conclude that adequate contact exists between the electrode 50 and the ablation site. When relying on such a finding, delay step 73 and step 74 may be omitted.

Control now proceeds to decision step 76, where it is determined if the temperature differential T2–T1 exceeds the above-noted predetermined threshold. If the determination at decision step 76 is affirmative, then control proceeds to final step 78. It is determined that the ablation electrode is in good contact with the target tissue. Success is reported to the operator, and ablation may continue.

If the determination at decision step 76 is negative then control proceeds to final step 80. The operator is alerted that the ablation electrode may not be in proper contact with the target tissue, which may cause him to interrupt the ablation by disabling the ablation power generator 25 and reposition the catheter.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method for treatment, comprising:
   bringing a probe into contact with a target tissue in a body of a subject, the probe having first and second temperature sensors on a distal portion of the probe and an ablation electrode thereon, the first and second temperature sensors being disposed on the distal portion, the second temperature sensor being spaced apart from the first temperature sensor such that when the ablation electrode is operationally engaged with the target tissue, the second temperature sensor is less responsive to heat generated at an ablation site comprising the target tissue than the first temperature sensor;
   applying energy through the ablation electrode to ablate the target tissue in the body;
   delivering coolant to the ablation electrode at a low coolant flow and a high coolant flow;
   reading the first and second temperature sensors in order to compute a temperature difference by computing a first temperature reading based on the respective temperatures sensed by the first temperature sensor and the second temperature sensor when the ablation electrode is cooled by the high coolant flow and a second temperature reading based on the respective temperatures sensed by the first temperature sensor and the second temperature sensor when the ablation electrode is cooled by the low coolant flow; and
   determining the contact to be sufficient for the treatment if the temperature difference between the first temperature reading and the second temperature reading is greater than a predetermined threshold.

2. The method according to claim 1, wherein the probe is a lasso catheter.

3. The method according to claim 1, wherein the first temperature sensor and the second temperature sensor are thermocouples.

4. The method according to claim 1, further comprising discontinuing applying energy when the temperature difference fails to exceed the predetermined threshold.

5. The method according to claim 1, wherein the probe is configured for insertion through a blood vessel into a heart of the subject for ablation of myocardial tissue in the heart.

* * * * *